United States Patent
Johnson et al.

(10) Patent No.: US 7,150,973 B2
(45) Date of Patent: Dec. 19, 2006

(54) METHODS AND KITS FOR PURIFYING HIS-TAGGED PROTEINS

(75) Inventors: Tonny Johnson, Madison, WI (US); Rebecca Godat, DeForest, WI (US); Laurie Engel, DeForest, WI (US)

(73) Assignee: Promega Corporation, Madison, WI (US)

( * ) Notice: Subject to any disclaimer, the term of this patent is extended or adjusted under 35 U.S.C. 154(b) by 0 days.

(21) Appl. No.: 11/032,281

(22) Filed: Jan. 10, 2005

(65) Prior Publication Data

US 2005/0209444 A1  Sep. 22, 2005

Related U.S. Application Data

(62) Division of application No. 10/840,408, filed on May 6, 2004.

(60) Provisional application No. 60/502,544, filed on Sep. 12, 2003.

(51) Int. Cl.
*G01N 33/53* (2006.01)
*C07K 1/00* (2006.01)
*C12P 21/06* (2006.01)

(52) U.S. Cl. ................ 435/7.1; 530/350; 435/69.1

(58) Field of Classification Search ............. 435/69.1, 435/7.1; 530/350
See application file for complete search history.

(56) References Cited

U.S. PATENT DOCUMENTS

| | | | |
|---|---|---|---|
| 5,840,851 A | 11/1998 | Plomer et al. | |
| 5,962,641 A | 10/1999 | Nelson et al. | |
| 6,232,083 B1 * | 5/2001 | Fisher et al. | ............ 435/7.1 |
| 6,242,581 B1 | 6/2001 | Nelson et al. | |
| 6,723,510 B1 | 4/2004 | Lubenow et al. | |
| 2004/0127357 A1 | 7/2004 | Simpson et al. | |

FOREIGN PATENT DOCUMENTS

| | | |
|---|---|---|
| WO | WO 98/06739 | 2/1998 |
| WO | WO 99/57992 | 11/1999 |
| WO | WO 02/37100 A2 | 5/2002 |

OTHER PUBLICATIONS

Lindner et al., Specific detection of his-tagged proteins with recombinant anti-His tag scFv-phosphatase or scFv-phage fusions. Biotechniques. Jan. 1997;(22)1:140-9.*

Heme protein/ Hemoprotein definition, Biocrawler; www.biocrawler.com/encyclopedia/Hemoprotein.*

Frenzel, A. et al., "Novel purification system for 6xHis-tagged proteins by magnetic affinity separation," Journal of Chromatography B (2003) 793:325-329.

BD Biosciences, Innovative Solutions for Proteomics, Clontech, Discovery Labware, Immunocytometry Systems, Pharmingen, 2002, 19 pages.

BD Biosciences, TALON™ Products For polyhistadime-tagged protein purification, 18 pages. (2002).].

Chaga, G., et al., "Immobilized metal ion affinity chromatography on $Co^{2+}$-carboxymethylaspartate-agrose Superflow, as demonstrated by one-step purification of lactate dehydrogenase from chicken breast muscle" *Biotechnol. Appl. Biochem.* 29:19-24 (1999).

Chisholm, et al., "Characterization of C-terminal histidine-tagged human recombinant lecitin:cholesterol acyltransferase" *J. Lipid Res.* Aug. 1999:40(8):1512-9.

Constans, A., "Protein Purification II: Affinity Tags" *The Scientist*, 16(4): 37 (Feb. 18, 2002).

Gupta, et al., "Immobilized Metal Affinity Chromatography without Chelating Ligands: Purification of Soybean Trypsin Inhibitor on Zinc Alginate Beads" *Biotechnol. Prog.* 18:78-81 (2002).

Gupta, G., et al., "Expression and purification of soluble, active heterodimeric guanylyl cyclase baculovirus" *Protein Expr Purif,* Aug.;10(3): 325-330 (1997).

Hansen, P. and G. Lindeberg, "Immobilized metal ion affinity chromatography of synthetic peptides—Binding via the α-amino group", *J. Chromatography*, 627:125-135 (1992).

Hengen, P.N., "Methods and reagents—Purification of His-Tag fusion proteins from *Escherichia coli*" Trends in Biochemical Sciences 20(7):285-286 (1995).

Hochuli, E., et al., "Genetic Approach to Facilitate Purification of Recombinant Proteins with a Novel Metal Chelate Adsorbent" *Bio/Technology*, 1321-1325 (Nov. 1988).

Hutchens, T.W and C.M. Li "Estrogen Receptor Interaction with Immobilized Metals: Differential Molecular Recognition of $Zn^{2+}$, $Cu^{2+}$, and $Ni^{2+}$ and Separation of Receptor Isoforms" *J. Molecular Recognition* 1(2): 80-92 (1988).

Hutchens, T.W. and T. Yip, "Protein Interactions with Immobilized Transition Metal Ions: Quantitative Evaluations of Variations in Affinity and Binding Capacity" *Analytical Biochemistry* 191: 160-168 (1990).

Hyun, et al., "Protein Adsorption on the Nickel-Coated Glass Slide for Protein Chips" *Bull. Korean Chem. Soc.* 23(12):1724-1728 (2002).

Jana et al., "Incorporation of cobalt and nickel metal nano-particles in nano-grain zirconia film matrix by solution route" *Bull. Mater. Sci.* 23(4):263-266 (2000).

Jodra Y. and F. Mijangos, "Ion exchange selectivities of calcium alginate gels for heavy metals" *Water Science & Technology* 43(2): 237-244 (2001).

(Continued)

*Primary Examiner*—Jon Weber
*Assistant Examiner*—Robert B. Mondesi
(74) *Attorney, Agent, or Firm*—Michael Best & Friedrich LLP

(57) ABSTRACT

Disclosed are methods of separating a target molecule from a non-target molecule using zinc- or cobalt-charged solid supports.

18 Claims, 12 Drawing Sheets

OTHER PUBLICATIONS

Kågedal, L., Proten Purification, Principles, High Resolution Methods, and Applications, Chapter 8 "Immobilized Metal Ion Affinity Chromatography" Jan-Crister Janson and Lars Rydén, eds. 227-251 (1989).

Lauer, S.A. and J.P. Nolan, "Development and Characterization of Ni-NTA-Bearing Microsphere" *Cytometry* 48:136-145 (2002).

Lehrer et al., "Putative protein markers in the sera of men with prostatic neoplasms" *BJU Int.* Aug.:92(3):223-225 (2002).

Littlejohn, T.K., et al., "Expression and Purification of Recombinant Human Indoleamine 2,3-Dioxygenase" *Protein Expression and Purification* 19: 22-29 (2000).

Piatibratov, M., et al., "Expression and fast-flow purification of a polyhistidine-tagged myoglobin-like aerotaxis transducer" *Biochimica et Biophysica Acta* 1524: 149-154 (2000).

Pierce Biotechnology, "ProFound™ Pull-down PolyHis Protein: Protein Interaction Kit" No. 21277, Jun. 2002, 14 pages.

Promega *In Vitro Resource*, Ch. 9, 58-61 (2000).

"Purification of His-tagged protein" http://www.biochem.ucl.ac.uk/~chen/protocols/histag.html Oct. 28, 2002.

Quan, L.T., et al., "Proteolytic activation of the cell death protease Yama/CPP32 by granzyme B" *PNAS USA*, 93: 1972-1976 (Mar. 1996).

Salih, B., et al., "Matrix-assisted Laser Desorption/Ionization Mass Spectrometry of Noncovalent Protein-Transition Metal Ion Complexes" *J. Mass Spectrometry*, 33:994-1002 (1998).

Schmidbauer, S.B. and O.K. Strobel "Purification of Histidine-tagged Fusion Protein Using POROS® Metal Chelate Perfusion Chromatography® Media: Rapid Method Optimization" *Biochemica* 3:22-24 (1997).

Sini, G. et al., "Preferential C-binding versus N-binding in Imidazole Depends on the Metal Fragment Involved" *Inorg Chem.* Feb. 11;41(3):602-4, (2002).

Volz, J., et al., "Molecular characterization of metal-binding polypeptide domains by electrospray ionization mass spectrometry and metal chelate affinity chromatography" *J. Chromatography A*, 800: 29-37 (1998).

Xenopore "Nickel Chelate Coated Microwell Plates for Binding Histidine Tagged Proteins and Peptides" http://www.xenopore.com/nickel_chelate_coated_microwell_.htm. [Date Unknown].

Yip, et al., "Evaluation of the Interaction of Peptides with Cu(II), Ni(II), and Zn(II) by High-Performance Immobilized Metal Ion Affinity Chromatography" *Analytical Biochemistry*, 183: 159-171 (1989).

Liu, "Molecular simulations to determine the chelating mechanisms of various metal ions to the His-tagged motif: A preliminary study" *Journal of Biomolecular Structure and Dynamics.* 21(1): 31-41 (Aug. 2003).

Jiang, et al., "Protein selectivity with immobilized metal ion-tacn sorbents: chromatographic studies with human serum proteins and several other globular proteins" *Analytical Biochemistry, Academic Press Inc.* New York, US 255: 47-58 (1998).

Godat, et al., "MagneHis™ Protein Purification System: Purification of His-Tagged Proteins in Multiple Formats" *Promega Notes No. 83* 2003.2-5.

HisTrap Kit Manual Produced by Aviator, printed by Wilkstroms, Sweden 1010336 (Feb. 2001) 1-24.

* cited by examiner

METHODS AND KITS FOR PURIFYING HIS-TAGGED PROTEINS

CROSS-REFERENCE TO RELATED APPLICATIONS

This application is a divisional of U.S. application Ser. No. 10/840,408, filed May 6, 2004, which claims the benefit of prior filed provisional patent application number 60/502,544 filed Sep. 12, 2003, each of which is incorporated herein by reference, in its entirety.

STATEMENT REGARDING FEDERALLY SPONSORED RESEARCH OR DEVELOPMENT

Not applicable.

INTRODUCTION

Histidine-tagged proteins are recombinant proteins designed to include a polyhistidine tail (his-tag) that facilitates purification of the proteins from in vitro expression systems. The preferential binding of the his-tag to metal chelating resins has been exploited in purifying his-tagged proteins from undesired contaminating proteins using immobilized metal affinity chromatography (IMAC). Metal chelating resins typically include a transition metal such as Ni or Co.

Like his-tagged proteins, heme proteins (e.g., hemoglobin or myoglobin) bind to metal chelating resins. When both his-tagged proteins and heme proteins are applied to a metal chelating resin, the heme proteins co-purify with his-tagged proteins. It is therefore difficult to separate his-tagged proteins from material containing heme proteins to obtain a preparation of his-tagged proteins of acceptable purity without a significant amount of contaminating heme proteins.

Rabbit reticulocyte lysate is a particularly useful expression system for obtaining expression of eukaryotic sequences. Rabbit reticulocyte lysate-based systems have been found to support co-translational and post-translational modifications of expressed proteins. However, because reticulocyte lysate includes large concentrations of hemoglobin, and because of the difficulties associated with separating hemoglobin from his-tagged proteins, reticulocyte lysate expression systems have not been fully exploited for expressing his-tagged proteins.

Lytton et al. (WO 02/37100 A2) discloses that removal of hemoglobin from his-tagged proteins produced in a rabbit reticulocyte lysate may be effected by first binding the hemoglobin and his-tagged proteins to a nickel nitrilotriacetic acid (Ni-NTA) resin in the presence of imidazole, followed by step-wise elution of hemoglobin and his-tagged proteins using an imidazole gradient.

There is a need in the art for simplified methods of separating heme proteins from his-tagged proteins that are amenable for use in high throughput systems.

SUMMARY OF THE INVENTION

In one aspect, the present invention provides methods for separating heme proteins from his-tagged protein in a starting material. The starting material is contacted with a zinc- or cobalt-charged solid support under conditions in which the support preferentially binds to his-tagged protein relative to its binding to hemoglobin. The conditions include no imidazole or imidazole in a concentration of from about 0 mM to about 60 mM. Suitably, imidazole may be present in a concentration of about 10 to about 40 mM, or from about 10 mM to about 20 mM.

In another aspect, the present invention provides kits for separating heme proteins from his-tagged proteins in a starting material. The kits include a zinc- or cobalt-charged solid support and a binding buffer that comprises no imidazole or imidazole in a concentration of from about 10 mM to about 60 mM. Optionally, the kits may further comprise an elution buffer comprising imidazole in a concentration from about 100 mM to about 3 M. In an alternative embodiment, the kits comprise an elution buffer comprising EDTA in a concentration of from about 10 mM to about 0.5 M, most suitably about 50 mM, or an elution buffer having a pH of less than about 6. The kits may further comprise instructions for performing the method according to the present invention.

DETAILED DESCRIPTION OF THE INVENTION

Figure 1:
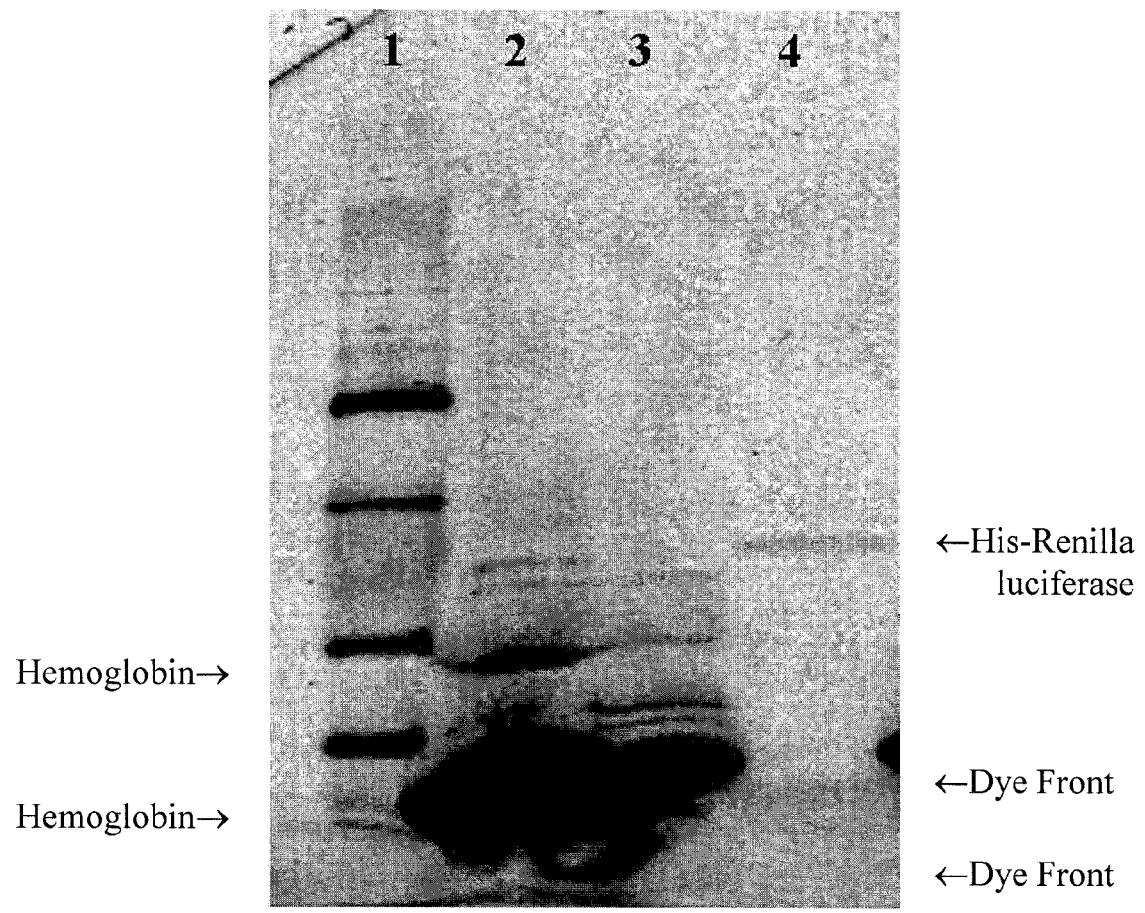
FIG. 1 shows a fluoroimage of electrophoretically separated proteins from rabbit reticulocyte lysate.

The present invention provides methods and kits for separating a heme protein from a target polypeptide in a sample comprising heme protein and the target polypeptide material using zinc- or cobalt-charged solid support. Suitably, the target polypeptide includes a polyhistidine tag of from five to six histidine residues.

The ability to separate heme proteins from a target protein of interest is particularly important in applications in which there are contaminating heme proteins, for example, when isolating proteins from reticulocyte lysate, from whole blood, or other bodily fluids or samples containing hemoglobin. Although purification schemes can be developed to separate virtually any proteins, such methods frequently require many steps and numerous reagents, are time- and labor-intensive, and are, therefore, not amenable to use in high throughput screening or assays.

As described in the Examples below, zinc- or cobalt-charged nitrilotriacetic acid (NTA) modified siliceous-oxide coated magnetic particles contacted with a sample comprising hemoglobin and his-tagged proteins in the absence of imidazole or in the presence of low levels of imidazole (10 to 60 mM) were found to preferentially bind to the his-tagged proteins, relative to binding of heme protein to the particles, such that an increase in purity of his-tagged protein from a hemoglobin-containing starting material was achieved. The term magnetic refers to paramagnetic particles, magnetic particles as well as particles capable of being magnetized. As described in the Examples, under conditions that allow preferential binding to his-tagged protein, hemoglobin binding to zinc- or cobalt-charged solid supports is minimal, whereas his-tagged proteins are bound with sufficiently high efficiency relative to similar supports charged with nickel. The methods of the invention afford an increase in purity of his-tagged proteins, relative to hemoglobin, of 1-fold or greater. Suitably, the increase in purity is least 2-fold, 2.5-fold, 5-fold, 10-fold, 20-fold, 50-fold, or 100-fold.

As one of skill in the art will appreciate, no purification scheme will result in 100% recovery of the desired protein or removal of 100% of undesired contaminants. Acceptable levels of hemoglobin contamination or recovery of target protein may vary, depending on the application. Conditions that allow preferential binding of his-tagged protein relative to hemoglobin suitably permit binding of less than 5% of hemoglobin present in the starting material, and at the same time permitting binding of at least some of the his-tagged protein. In some applications, less than 1% of the hemoglobin present in the starting material binds to the solid support, or even as little 0.5% or 0.1% or less of the hemoglobin present in the starting material binds to the solid support. Thus, a substantial increase in purification of his-tagged proteins can be achieved using the zinc- or cobalt-charged solid supports.

This result is surprising in view of the teachings of the prior art, which discloses methods for immobilizing hemoglobin on a nickel-NTA resin using 10 to 20 mM imidazole (Lytton et al., WO 02/37100). In contrast, in the method of the present invention, the starting material containing hemoglobin and his-tagged proteins is contacted with a zinc- or cobalt-charged solid support in the absence of imidazole or in the presence of 10 to 60 mM imidazole, conditions that allow preferential binding of his-tagged proteins to the resin, relative to binding of hemoglobin to the resin.

Siliceous oxide-coated magnetic particles modified with nitrilotriacetic acid (NTA) to produce 3-[[[bis(carboxymethyl)amino]acetyl]amino]-propyl magnetic silica particles (NTA-modified magnetic silica particles), as described in U.S. application Ser. No. 10/689,176, filed Oct. 20, 2003, were used in the Examples below. However, as one skilled in the art will appreciate, the method is not intended to be limited to use with the particles exemplified below, but rather, is believed to have general applicability for use with any suitable zinc- or cobalt-charged solid support.

It is specifically envisioned that, in addition to silica magnetic particles used in the examples, other types of solid supports may be used in the methods of the invention, including, but not limited to, silica gel, siliceous oxide, solid silica such as glass or diatomaceous earth, agarose, polyacrylamide, cellulose, plastic, polysaccharide, nylon, polystyrene, or latex methacrylate.

In addition to solid supports modified to include the particular NTA linkage used below in the Examples (i.e., 3-[[[bis(carboxymethyl)amino]acetyl]amino]-propyl magnetic silica particles), it is envisioned that NTA may be linked to a solid support by other means and used in the method of the invention. In addition to NTA, other types of metal chelating ligands, including, but not limited to, iminodiacetate (IDA) or Tris(carboxymethyl)ethylendiamin ligand (TED), for example, may be used in the practice of the invention.

It is also envisioned that zinc or cobalt could be attached covalently or noncovalently to a solid support without using a chelating agent. For example, a solid support could be coated with zinc or cobalt. Any suitable method for coating the solid supports with a metal such as zinc or cobalt may be used (e.g., see Hyun et al. Bull. Korean Chem. Soc. 23:1724–1728, 2002). Gupta et al. describe attaching zinc directly to alginate beads without the use of a chelating agent (Biotechnol. Prog. 18:78–81, 2002). Another approach for attaching zinc or cobalt to the solid support is to incorporate the metal into the matrix of the support (Jana et al. Bull. Mater. Sci. 23:263–266, 2000).

In the Examples below, immobilized his-tagged proteins were eluted from the particles using imidazole (500 mM). As one of skill in the art will appreciate, immobilized his-tagged proteins may be eluted using other suitable buffers comprising imidazole in the range of from about 100 mM to about 3M imidazole. As one skilled in the art would appreciate, the conditions selected may vary according to the particular protein and the objective (e.g., enhancing yield or purity). Immobilized his-tagged proteins may be eluted using a suitable buffer having a pH of less than about 6.5 to enhance yield. To minimize imidazole inhibition in downstream applications or background associated with high imidazole elutions, an elution buffer of histidine (e.g., 100 mM histidine) or 500 mM potassium acetate and 50 mM EDTA may be used. Buffers containing EDTA in a concentration of from about 10 mM to about 0.5 M are also suitable.

A his-tagged *Renilla luciferase*, HGF, MAPK, calmodulin, and Id were used to demonstrate the efficacy of the method in purifying his-tagged proteins from hemeproteins. However, the methods of the invention have general applicability to any his-tagged protein. His-tags may be at the carboxy or amino terminus and are typically five or six histidine residues in length, but may be longer.

The methods of the invention may be used for high throughput purification of his-tagged proteins expressed in rabbit reticulocyte lysate, by expressing cDNA libraries containing his-tagged proteins followed by isolating the proteins according to the methods of the invention.

Rabbit reticulocyte is widely used for expressing post-translationally modified proteins, such as glycosylated proteins. Using the methods disclosed herein, one may obtain preparations of modified protein from rabbit reticulocyte lysate with very little hemoglobin contamination.

It is envisioned that his-tagged proteins expressed and subsequently purified by the method of the invention are suitable for subsequent evaluation by mass spectrometry analysis.

As described in the Examples below, zinc or cobalt charged solid supports are useful in a variety of applications in addition to isolating his-tagged proteins. For example, his-tagged proteins purified using zinc or cobalt charged solid supports are suitable for subsequently detecting interactions between the his-tagged proteins and other substances, including substrates (e.g., detecting the ability of the his-tagged protein to function as a kinase or protease) and other proteins (e.g., detecting the ability of his-tagged proteins to serve as a substrate for a kinase or protease). In addition, simple protein-protein interactions and antigen-antibody binding involving the his-tagged proteins may be detected. Such activity or interactions may be evaluated by any suitable means.

Contaminating hemoglobin ordinarily present in rabbit reticulocyte lysate typically interferes with fluorescent or luminescent based assays, in part because hemoglobin itself fluoresces and may mask the signal of a low expressing protein. Because most of the hemoglobin present in rabbit reticulocyte lysate or blood is removed during purification steps according to the present invention, interactions or activity may be conveniently detected using fluorescent or luminescent means without significant interference from hemoglobin.

The following non-limiting examples are intended to be purely illustrative.

EXAMPLE 1

Preparation of Zinc- or Cobalt-Charged Nitrilotriacetic Acid-Modified Magnetic Silica Particles Siliceous oxide-coated magnetic particles were modified with nitrilotriacetic acid (NTA) to produce 3-[[[bis(carboxymethyl)amino]acetyl]amino]-propyl magnetic silica particles (NTA-modified magnetic silica particles), as described in U.S. application Ser. No. 10/689,176, filed Oct. 20, 2003, which is incorporated by reference in its entirety.

Zinc-charged particles were prepared as follows. Particles in a 4-ml aliquot of NTA-modified particles (10% w/v in water) were separated from the liquid using magnetization and the liquid discarded. The particles were contacted with 4 ml of ZnCl (100 mM) and rocked on a horizontal shaker (5–10 rpm) for 15 minutes. The particles were separated from the liquid using magnetization and the liquid discarded. The particles were contacted with a fresh 4-ml aliqout of ZnCl (100 mM), rocked on a horizontal shaker (5–10 rpm) for 15 minutes, and the particles were separated from the ZnCl solution using magnetization. The particles were washed with 4 ml of nanopure water and rocked on a horizontal shaker (5–10 rpm) for 5 minutes. The particles were separated from the water using magnetization and the liquid discarded. The wash step was repeated 10 times. After the final wash, 4 ml of nanopure water was added to the particles, and the particles were stored at 4° C. until use.

Cobalt-charged particles were prepared as follows. Particles in a 4-ml aliquot of NTA-modified particles (10% w/v in water) were separated from the liquid using magnetization and the liquid discarded. The particles were contacted with 4 ml of $CoCl_2$ (100 mM) and rocked on a horizontal shaker (5–10 rpm) for 15 minutes. The particles were separated from the liquid using magnetization and the liquid discarded. The particles were contacted with a fresh 4-ml aliquot of $CoCl_2$ (100 mM) and rocked on a horizontal shaker (5–10 rpm) for 15 minutes. The particles were separated from the $CoCl_2$ solution using magnetization. The particles were washed with 4 ml of nanopure water and rocked on a horizontal shaker (5–10 rpm) for 5 minutes. The particles were separated from the water using magnetization and the liquid discarded. The wash step was repeated 10 times. After the final wash, 4 ml of nanopure water was added to the particles, and the particles were stored at 4° C. until use.

EXAMPLE 2

Expression of his-Tagged Proteins in Rabbit Reticulocyte Lysate Using Coupled Transcription/Translation An expression vector encoding his-tagged *Renilla luciferase* was expressed using TNT® T7 Quick Coupled Transcription/Translation System, Cat# L1170TNT (Promega Corp., Madison, W.I.) according to the manufacturer's instructions.

EXAMPLE 3

Purification of his-Tagged Proteins from Rabbit Reticulocyte Lysate

His-tagged *Renilla luciferase*, prepared as described in Example 2, was purified from the coupled transcription/translation reaction mixture as follows. A 50-µl aliquot of the reaction mixture was combined with 150-µl binding buffer A (sodium phosphate buffer 100 mM, imidazole 20 mM, and NaCl 400 mM) buffered at a pH in the range of 6.0 to 8.0, and combined with 30 µl (3 mg) of zinc charged particles, prepared as described in Example, for 15—15 minutes at room temperature. The particles were separated from the solution ("flowthrough solution") using magnetization, and the particles were washed with 200 µl binding buffer three to five times. Proteins were eluted by thoroughly mixing the particles with 100 µl elution buffer (HEPES 100 mM (pH 7.5) and imidazole 500 mM), separating the particles from the elution buffer by magnetization, and collecting the eluted proteins.

EXAMPLE 4

Evaluation of Proteins

Proteins present in the elution prepared as described in Example 3 above were evaluated using SDS-PAGE and fluorescence scanning or Western blot analysis. Results are shown in FIG. 1–4, as described below.

FIG. 1 shows a fluorescent scan of electrophoretically separated proteins. Lane 1 contains fluorescently-labeled molecular weight markers; lane 2 contains proteins in untreated lysate reaction mixture following expression of *Renilla luciferase*, as described in Example 2; lane 3 contains the flowthrough solution of lysate reaction mixture combined (1:3) with binding buffer buffered at pH 7.5, as described in Example 3, above; and lane 4 contains the eluate from Example 3 above. Bands corresponding to hemoglobin, his-tagged *Renilla luciferase*, or the dye front are indicated on the scan. As can be seen by comparing lanes 3 and 4, the purification step results in a substantial increase in the purity of the his-tagged protein.

Figure 2:
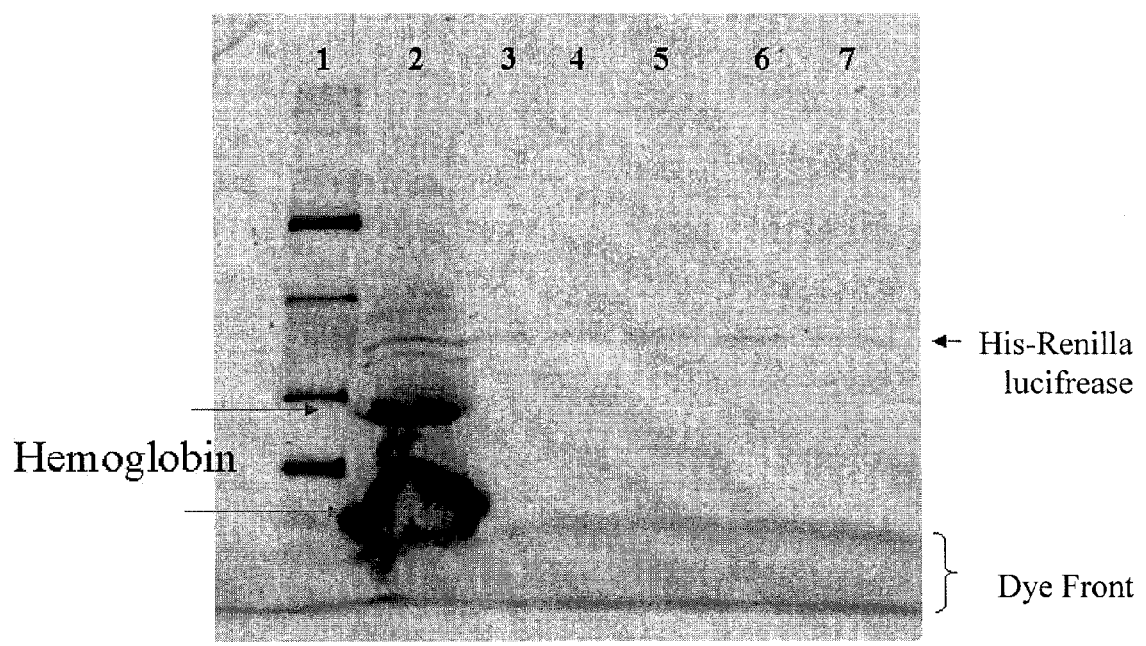
FIG. 2 shows a fluoroimage of electrophoretically separated proteins from rabbit reticulocyte lysate.

With reference to FIG. 2, which shows a fluorescent scan of proteins, lane 1 contains fluorescently-labeled molecular weight markers, lane 2 contains proteins in untreated lysate following expression of *Renilla luciferase*, as described in Example 2, and lanes 3–7 contain proteins that were first bound to the support with binding buffer buffered at pH 6.0, 6.5, 7.0, 7.5, or 8.0, respectively, and then eluted with elution buffer. Bands corresponding to hemoglobin, his-tagged *Renilla luciferase*, or the dye front are indicated on the scan. As can be seen from the absence of bands intense bands corresponding in size to hemoglobin and the presence of strong bands corresponding in size to his-tagged *Renilla*

*luciferase* in lanes 3–7, a substantial increase in the purity of the his-tagged protein was effected.

Figure 3:
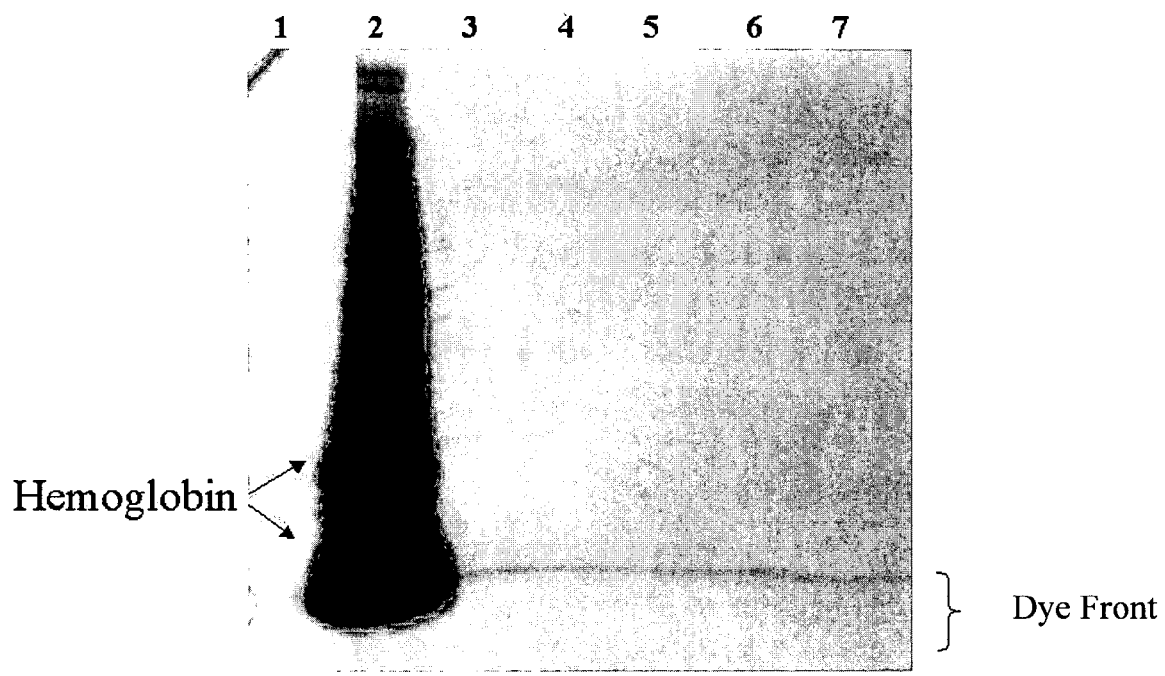
FIG. 3 shows proteins from rabbit reticulocyte lysate separated by SDS-PAGE and stained with GELCODE™ Blue Stain Reagent, product No. 24592 (Pierce Chemicals, Rockford, IL).

FIG. 3 shows a SDS-PAGE gel stained with GELCODE™ Blue Stain Reagent, product No. 24592 (Pierce Chemicals, Rockford, IL), including molecular weight markers (lane 1), untreated lysate reaction mixture (lane 2), and proteins eluted with elution buffer following binding to the solid support with binding buffer buffered at pH 6.0, 6.5, 7.0, 7.5, or 8.0 (lanes 3–7, respectively). This gel demonstrates that the amount of his-tagged *Renilla luciferase* and hemoglobin contaminant in the eluate (lanes 3–7) is below the limits of detection of this system.

Figure 4:
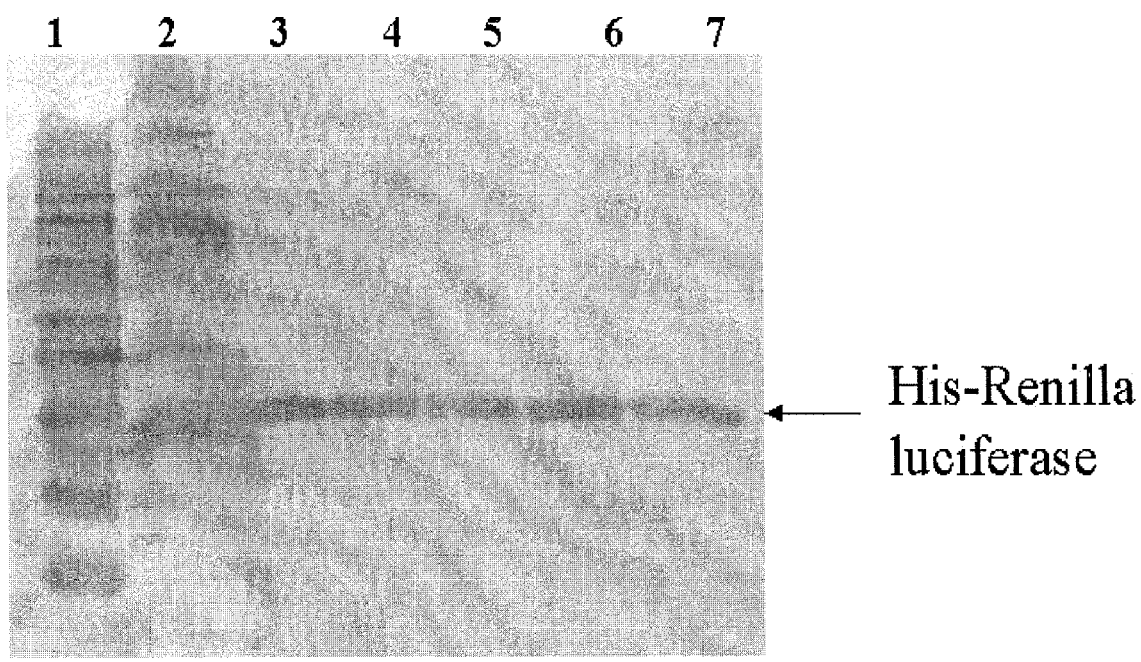
FIG. 4 shows Western blot of electrophoretically separated proteins from rabbit reticulocyte lysate probed with anti-*renilla luciferase* antibody.

FIG. 4 shows a Western blot of electrophoretically separated proteins probed with anti-*Renilla luciferase* antibody, including molecular weight markers (lane 1), lysate (lane 2), and proteins eluted with elution buffer following binding to a solid support with binding buffer buffered at pH 6.0, 6.5, 7.0, 7.5, or 8.0 (lanes 3–7, respectively). Non-specific binding of the antibody to proteins in the lysate, as well as specific binding to his-tagged *Renilla luciferase*, can be seen in the lysate in lane 2. In contrast, binding of the anti-*Renilla luciferase* antibody in lanes 3–7 is limited to a protein having a size consistent with that of his-tagged *Renilla luciferase*.

Figure 5:
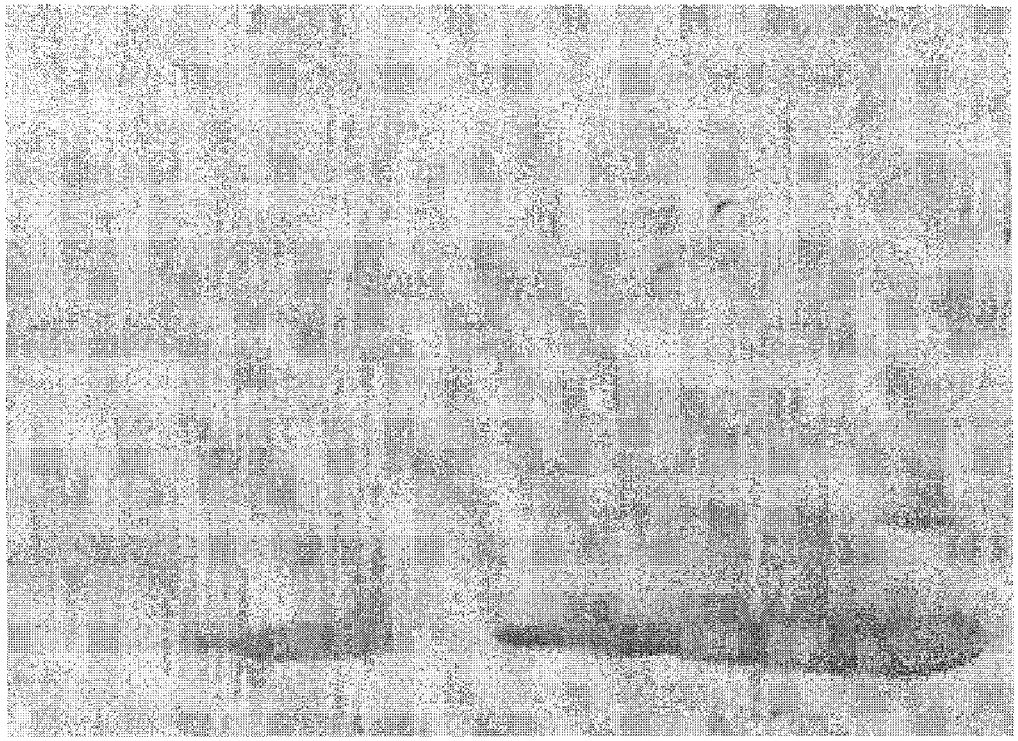
FIG. 5 shows a Western blot of proteins from rabbit reticulocyte lysate electrophoretically separated by SDS-PAGE and probed with anti-hemoglobin antibody.

FIG. 5 shows a Western blot of proteins found in rabbit reticulocyte lysate treated as described below and probed with anti-hemoglobin antibody. Lane 1: A 50 µl aliquot of rabbit reticulocyte lysate was mixed with 100 µl of binding/wash buffer B as described below in Example 5 (20 mM sodium phosphate buffer (pH 7.5) and 500 mM NaCl) and incubated with 60 µl zinc particles (5% w/v) for 15 min on orbital rocker. The particles were washed 4 times with 200 µl of binding/wash buffer and eluted with 100 µl of elution buffer (1M imidazole). Lane 2: A 50 µl aliquot of rabbit reticulocyte lysate was mixed with 100 µl of binding/wash buffer B, mixed by pipeting with incubated with 30 µl MagneHis™ nickel particles (10% w/v) (Catalog # V8500, Promega Corp.). The particles were washed 3 times with 150 µl of binding/wash buffer and eluted with 100 µl of elution buffer (500 mM imidazole). Lanes 3–8 contain lysate not contacted with particles and diluted to from 0–5% of the original lysate concentration. Lanes 3–8 contain 0, 0.15, 0.6, 1.25, 2.5, 5 percent lysate, respectively. Sheep anti-human hemoglobin-AP 1:1000 was used to probe the Western blot, and binding of the sheep anti-human hemoglobin-AP 1:1000 was detected Western blue stabilized substrate for alkaline phosphatase (S3841).

EXAMPLE 5

Differential Binding of His-Tagged Proteins in the Absence of Imidazole

The ability of his-tagged proteins to preferentially bind to a zinc charged solid support in the absence of imidazole was evaluated in an experiment parallel to that described in Example 3. His-tagged proteins (His-calmodulin, His-MAPK, his-HGF) were expressed using TNT® T7 Quick Coupled Transcription/Translation System, Cat# L1170TNT (Promega Corp., Madison, WI), 1 µg DNA, and 2 µl FLUOROTECT™ Green$_{LYS}$ in vitro Translation Labeling System (Cat. # L5001). A 50-µl aliquot of the reaction mixture was combined with 100-µl binding buffer B (20 mM sodium phosphate buffer (pH 7.5) and 500 mM NaCl), transferred to a 0.5 or 1.5 ml tube with a 60 µl(6 mg) of zinc charged particles (prepared as described in Example 1), and gently mixed for 15 minutes at room temperature. The particles were separated from the solution using magnetization, and the particles were washed with 200 µl of binding buffer three to five times. Proteins were eluted by thoroughly mixing the particles with 100 µl elution buffer (1 M imidazole (pH 7.5)), separating the particles from the elution buffer by magnetization, and collecting the eluate.

Figure 6:
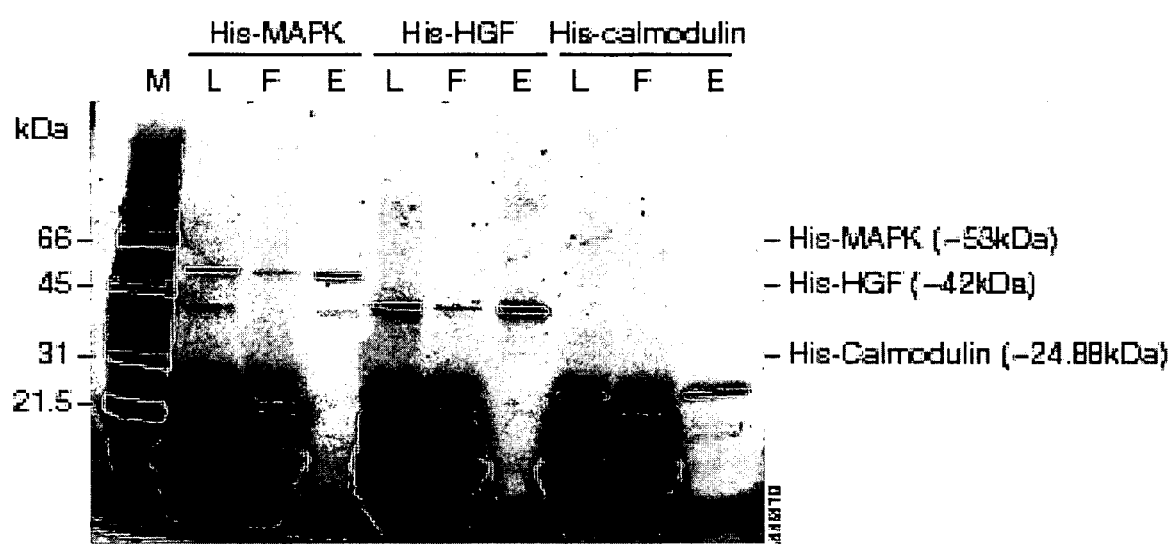
FIG. 6 shows a fluorescent scan of electrophoretically separated proteins.

Proteins present in the eluate prepared as described above were evaluated using SDS-PAGE and fluorescence scanning or Western blot analysis. FIG. 6 shows a fluorescent scan of electrophoretically separated proteins. Lane 1 contains fluorescently-labeled molecular weight markers; lane 2 contains proteins in 2 µl untreated lysate reaction mixture following expression of His-MAPK; lane 3 contains 6 µl the flowthrough solution of lysate reaction mixture combined (1:2) with binding buffer; and lane 4 contains 8 µl the eluate, as described above; lane 5 contains proteins in 2 µl untreated lysate reaction mixture following expression of His-HGF; lane 6 contains 6 µl the flowthrough solution of lysate reaction mixture combined (1:2) with binding buffer; lane 7 contains 8 µl the eluate; lane 8 contains proteins in 2 µl untreated lysate reaction mixture following expression of His-calmodulin; lane 9 contains 6 µl the flowthrough solution of lysate reaction mixture combined (1:2) with binding buffer; and lane 10 contains 8 µl the eluate.

EXAMPLE 6

Detecting Protein-Protein Interactions using Protein Pull Down Assays

The zinc-charged solid support system described above was evaluated for the ability isolate an untagged polypeptide of interest ("prey") from other non-target molecules using a his-tagged protein ("bait") using MyoD as the prey protein and Id as the bait protein as described below. MyoD and Id are members of the helix-loop-helix family of nuclear proteins. MyoD is a myogenic regulatory protein expressed in skeletal muscle, and Id protein is a negative regulator of myogenic differentiation that interacts with MyoD.

Untagged MyoD prey protein was expressed in TNT® T7 coupled transcription/translation lysate (Cat#L1170, Promega Corp.), 1µg of MyoD DNA and 2µl of 35S methionine as recommended in the Technical Bulletin (Cat#L1170, Promega His-tagged Id was expressed in an *E. coli* expression system according to standard protocols. Following expression, the cultured bacteria were pelleted, resuspended at a 10× concentration, and sonicated to form a bacterial lysate. The His-Id was also expressed in a TNT T7 coupled transcription/translation lysate (Cat#L1170, Promega Corp., Madison, WI).

Zinc charged solid support with bound his-tagged Id was prepared as follows. A 100 µl aliquot of 10× concentrated lysate containing the his-tagged Id bait was added to 30 µl zinc-charged NTA-modified magnetic silica particles and incubated for 15 minutes on a shaker 1100 rpm. The particles were washed three times with 200 µl of 20 mM sodium phosphate, pH 7.4. The particles were resuspended in 30 µl of buffer, and 5 µl aliquots of the particles were transferred to new tubes. One set of samples was washed twice with 20 mM sodium phosphate +40 mM imidazole and a second set was washed twice with 20 mM sodium phosphate. The particles were resuspended in the wash buffer (175 µl) and incubated at 30° C. for 60 minutes with gentle rocking.

A 20 µl aliquot of TNT® lysate containing MyoD was combined with the zinc solid support-bound his-Id and incubated for at room temperature for 60 minutes with gentle agitation. The particles were washed three times in the same final wash buffer used during preparation of the immobilized his-tagged Id, followed by a washing with 20 mM sodium phosphate and an additional wash of 40 or 500 mM imidazole. 20 μl of SDS buffer (0.24 M Tris-HCl (pH 6.8), 2% SDS, 3 mM bromophenol blue, 50.4% glycerol, and 0.4 M dithiothreitol) was added to the particles, incubated for 5 minutes with shaking and the sample was collected. The elution sample was diluted 1:10 in SDS buffer, heated at 95° C., and loaded onto 4–20% tris-glycine gel. The gel was transferred to PVDF membrane, exposed to phosphorimager plate overnight, and read on a STORM™ Phosphorimager (Amersham Biosciences, Piscataway, N.J.).

Isolation of a "prey" protein co-expressed with the bait protein was compared with isolation of a prey protein expressed separately from the bait protein. Both his-tagged Id and untagged MyoD proteins were expressed in two different TNT® reactions or co-expressed in the same TNT® lysate. When the his-Id and MyoD were expressed in separate reactions, equal volumes of his-Id expressing lysate and MyoD expressing lysate were mixed. Zinc-charged NTA-modified magnetic silica particles were added and processed as described above.

Figure 7:
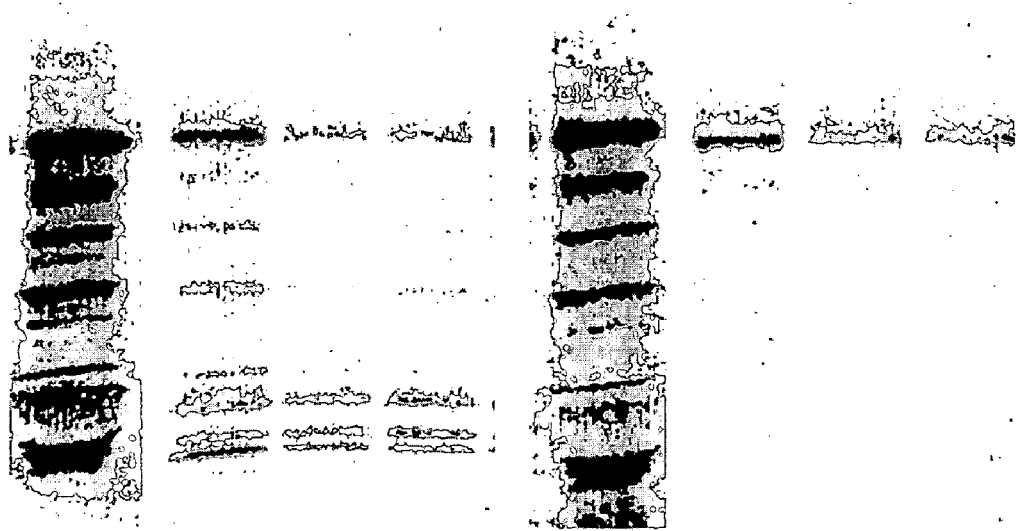
FIG. 7 is an image of electrophoretically separated proteins.

With reference to the image shown in FIG. 7, lanes 1 and 5 include the lysate of a TNT® expression system expressing 35S labeled MyoD; lanes 2 and 6 include his-Id bound to zinc-charged solid support and MyoD; 3 and 7 include his-RNaseH bound to zinc charged NTA-modified magnetic silica particles and MyoD; and lanes 4 and 8 include MyoD eluted from zinc charged NTA-modified magnetic silica particles in the absence of his-ID. Prior to elution, protein in lanes 1–4 was washed with 500 mM imidazole, and protein in lanes 5–8 was washed with 40 mM imidazole.

The results indicate that his-tagged proteins associated with zinc charged NTA-modified magnetic silica particles can be used to isolate a second protein that interacts with the his-tagged protein. Efficiency of recovery of MyoD is greatly enhanced by the presence of his-Id. Washing with imidazole at concentrations of 40 mM or greater was found to give acceptable results, with increasing concentrations of imidazole in the wash reducing the background.

Figure 8:
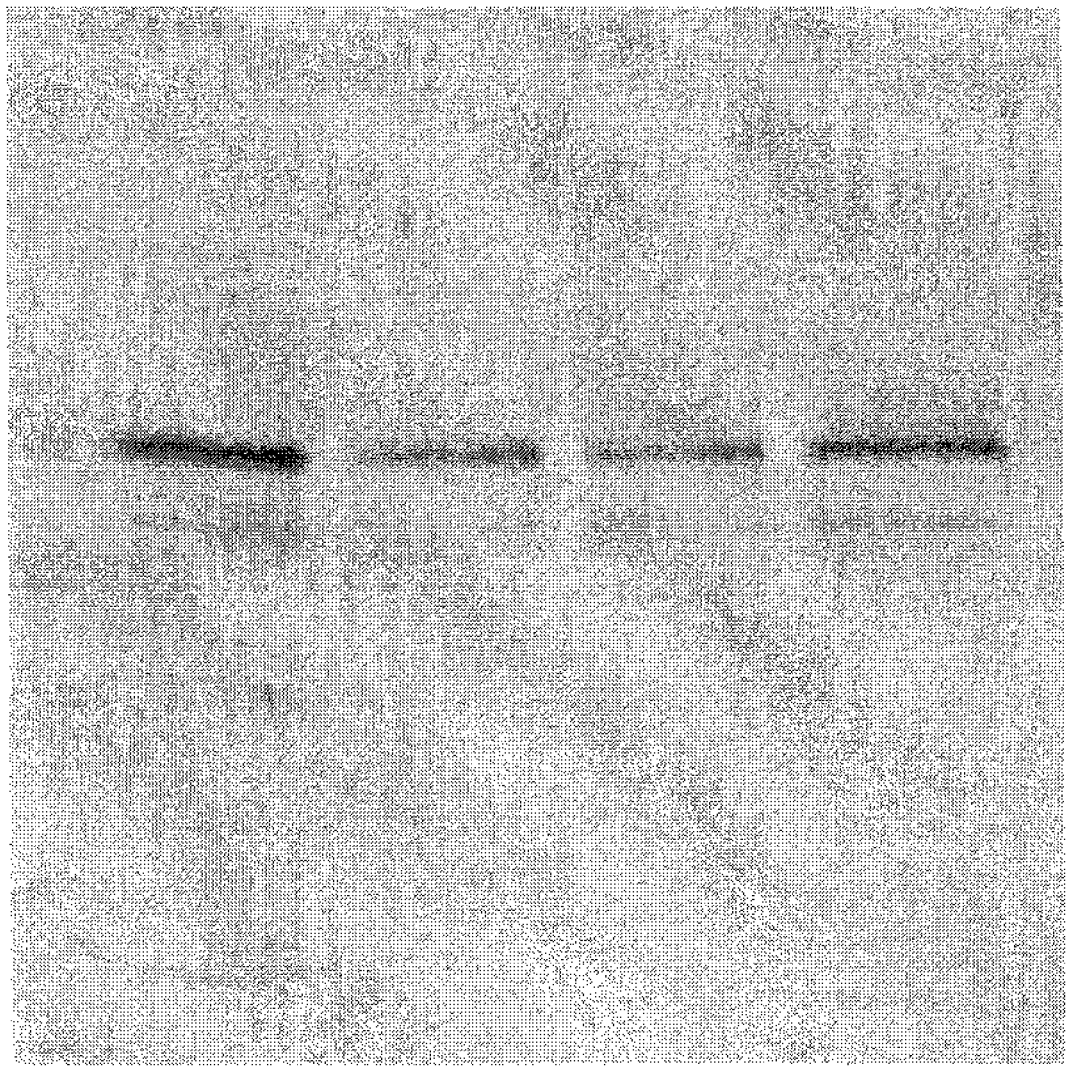
FIG. 8 is a Western blot of electrophoretically separated proteins.

The results were verified using Western analysis, with anti-MyoD antibody (FIG. 8). Lane 1 includes a rabbit reticulocyte lysate expressing untagged $^{35}$S MyoD; lane 2 shows the proteins isolated using zinc charged silica magnetic particles; lane 3 shows protein isolated using His-RNaseHI associated zinc charged silica magnetic particles; and lane 4 shows proteins isolated using His-Id associated zinc charged silica magnetic particles.

EXAMPLE 7

Detecting Protein-Protein Interactions of Co-Expressed Proteins

His-tagged bait protein (his-Id) and prey protein (MyoD) were co-expressed in TNT® T7 coupled transcription/translation lysate (Cat#L1170, Promega Corp., Madison, W.I.) and radiolabeled with $^{35}$S. A 60 μl aliquot of zinc particles (5% w/v) or 30 μl of nickel MAGNEHIS™ resin (10% w/v) (Promega Cat# V8500) was added to a 1.5 ml tube wash with 200 μl of 20 mM sodium phosphate buffer pH 7.4 and resuspended in 60 μl of 20 mM sodium phosphate buffer. A 5 μl aliquot of resin was mixed with 145 μl of 20 mM sodium phosphate in a 1.5 ml tube. 50 μl of TNT® reaction was added to resin and incubated for 1 hr at room temperature on orbital rocker. The supernatant was removed, and the resin was washed 4 times with 200 μl of 20 mM sodium phosphate +40 mM imidazole, pH 7.4. The proteins were eluted by mixing the resin with 20 μl 4×SDS buffer for 5 min. The elution was collected and a 2 μl aliquot was mixed with 18 μl 4×SDS buffer and run a SDS-PAGE gel. The electrophoretically separated proteins were transferred to PVDF and exposed to phosphorimager plates overnight (FIG. 9).

Figure 9:
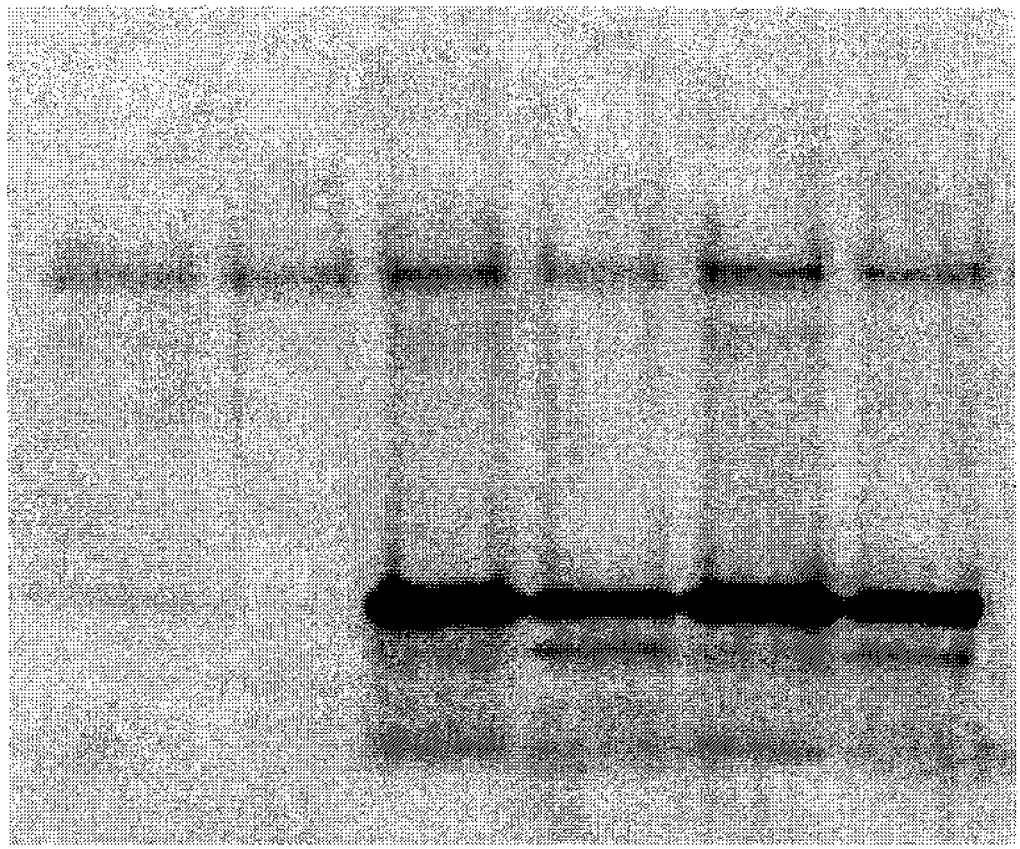
FIG. 9 is an image of electrophoretically separated proteins.

With reference to FIG. 9, lane 1 includes MyoD control (0.5 μg DNA); lane 2 contains MyoD control 1.0 μg DNA; lane 3 includes MyoD and his-Id from reticulocyte lysate programmed with 1.0 μg DNA isolated using zinc particles; lane 4 includes MyoD and his-Id from reticulocyte lysate programmed with 1.0 μg DNA isolated using nickel particles; lane 5 includes MyoD and his-Id from reticulocyte lysate programmed with 0.5 μg DNA isolated using zinc particles; lane 6 includes MyoD and his-Id from reticulocyte lysate programmed with 0.5 μg DNA isolated using nickel particles.

The results indicate co-expressed proteins can be used for the pull down experiments using a zinc-charged solid support, and that zinc charged solid support affords greater yield than nickel charged resin (FIG. 9).

EXAMPLE 8

High Throughput Purification of his-Tagged Proteins

A cDNA library coding for his-tagged proteins is expressed using GOLD TNT® SP6 Express 96 System (Promega Cat#L5800) or GOLD TNT® T7 Express 96 System (Promega Cat#L5600) for expressing the his-tagged proteins as recommended by the manufacturer. Expressed his-tagged protein are purified using a zinc or cobalt charged solid support in conjunction with a robotic system, including a suitable robot such as KINGFISHER® (Thermo Labsystems, Waltham, M.A.), BIOMEK® 2000 or BIOMEK® FX (Beckman Coulter, Inc., Fullerton, C.A.). An automated purification of his-tagged proteins in general is described in Technical Manual #TM060 (Promega Corporation).

EXAMPLE 9

Mass Spectrometry Analysis of his-Tagged Proteins

His-tagged proteins expressed in rabbit reticulocyte are purified as essentially as described in Example 3 or 5, except that, following the final wash, the his-tagged proteins are eluted with an elution buffer containing 0.1% TFA in water or in 50% acetonitrile. Following elution, protein samples are dried in a SPEED VAC™ and analyzed in MALDI-TOF mass spectrometer.

EXAMPLE 10

Expression and Purification of his-Tagged Membrane Proteins

His-tagged human cytochrome P450, subfamily IIIA, polypeptide 7 (CYP3A7) (Cat# E01046, Stratagene, LaJolla, C.A.) is expressed in Rabbit Recticulocyte TNT® with Canine Pancreatic Microsomal Membrane (Promega Cat# Y40141) according to manufacture's protocol. The his-tagged protein is purified directly from the lysate as described in Example 3 or 5. The expressed protein is also purified after solubilizing the expressed membrane protein in presence of a non-ionic detergent like 1,2-Dihexanoyl-sn-Glycero-3-Phosphocholine (DHPC, Cat# 850305C, Avanti Polar Lipids, Alabaster, L.A.). Functional analysis of the expressed and purified his-human cytochrome P450, subfamily IIIA, polypeptide 7 is performed by P450-GLO™ CYP3A7 Assay (Promega Cat# V8811).

Zinc-charged solid supports may be used to purify other membrane proteins expressed in rabbit reticulocyte lysate. For example, G-protein coupled receptors (GPCR) are expressed in TNT® with canine microsomal membranes or phospholipids. The GCPR is purified on zinc-charged solid supports using non-ionic detergents for use in ligand binding assays.

Figure 10:
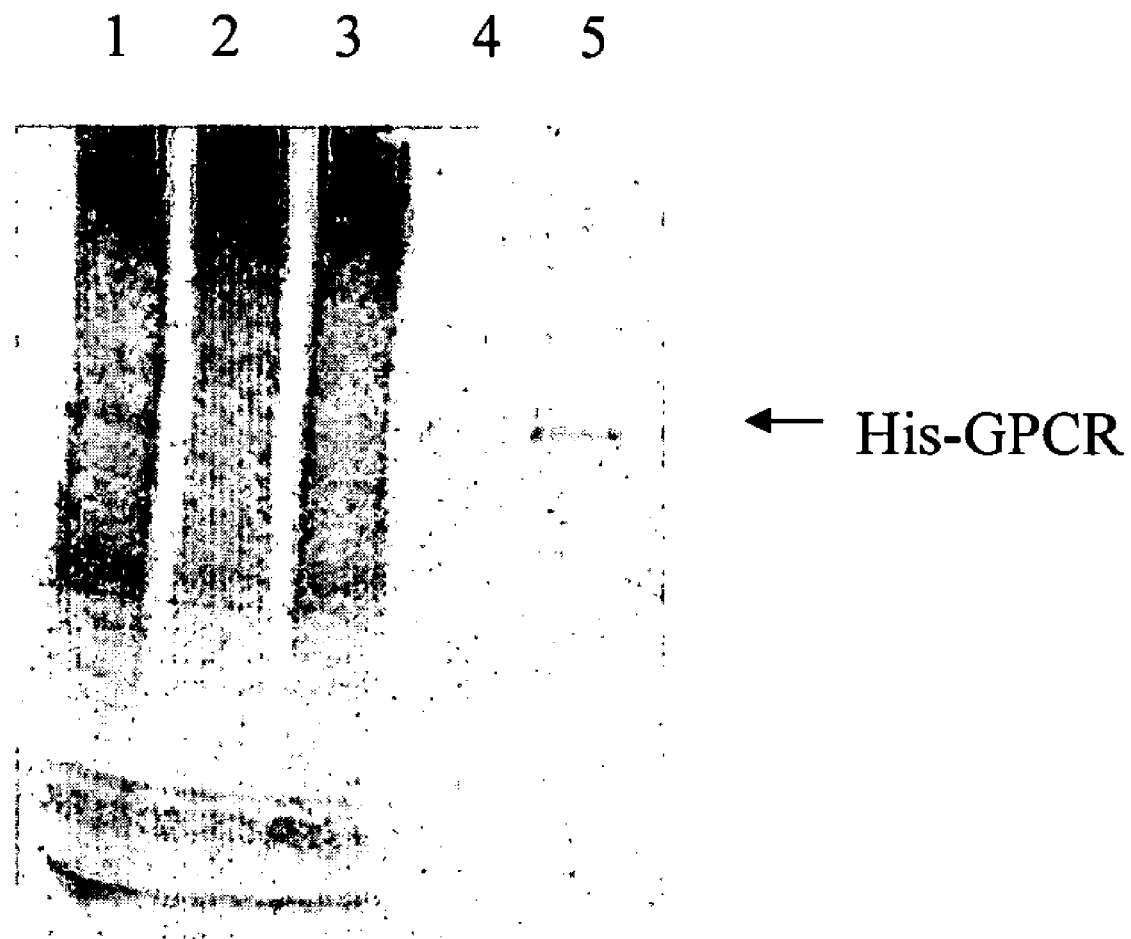
FIG. 10 is an image of electrophoretically separated proteins.

For proof of concept, a his-tagged GPCR (formyl peptide receptor) was selected. The protein was expressed in TNT T7 coupled transcription/translation lysate (Cat#L1170, Promega Corp., Madison, W.I.) using $^{35}S$ labeling as described above, and purified essentially according to Example 5. The lysate was contacted with 60 or 180 µl zinc charged magnetic silica particles (5% w/v), the particles washed, and the proteins eluted and analyzed by SDS-PAGE (FIG. 10). With reference to FIG. 10, lane 1 contains TNT® lysate expressing the his-GPCR; lane 2 contains flow through of 60 µl particles; lane 3 contains flow through of 18011 resin; lane 4 contains eulution from 60 µl particles; and lane 5 contains elution from 180 µl resin.

EXAMPLE 11

Expression, Purification and Analysis of Glycosylated his-Tagged Proteins

His-tagged glycoprotein is expressed in rabbit reticulocyte TNT® with Canine Pancreatic Microsomal Membrane (Promega Cat# Y40141) according to manufacture's protocol, purified as described above, and analyzed by SDS-PAGE, by Western blot, or by mass spectrometry to determine N-linked glycosylation.

EXAMPLE 12

Functional Screening for Kinases and Kinase Substrates

A his-tagged cDNA library is expressed in GOLD TNT® (Promega Cat. # L5800) or in PROTEOLINK™ In Vitro Expression Cloning System (adult human brain cDNA) (Promega, Cat# L6500). The his-tagged proteins are purified from heme proteins by contacting with a zinc-charged solid support (e.g., NTA-modified silica magnetic particles), followed by washing, as described above. Kinase activity is assayed with the his-tagged proteins bound to the solid support or after eluting the proteins. Because the bound or eluted his-tagged proteins are essentially free of heme proteins, a fluorescence based assay may be used to detect kinase activity using either eluted his-tagged proteins or his-tagged proteins bound to the resin. Kinase assay may also be performed using the KINASE-GLO™ Luminescent Kinase Assay (Promega, Cat# V6711). Other protein kinase substrates that may be used to detect kinase activity are available from EMD Biosciences, Inc. (Madison, W.I.).

The kinases or kinase substrates identified as described above may be cloned as described in the manufacturer's protocol.

EXAMPLE 13

Characterization of Genes and Proteins by Tandem Mass Spectrometry

A cDNA library encoding his-tagged proteins is expressed as described in above and the his-tagged proteins are purified by the methods described in Examples 3, 5, or 7. Purified proteins are digested with Trypsin Gold, Mass Spectrometry Grade (Promega, Cat# V5280) and the peptides are characterized by tandem mass spectrometry. Polynucleotides encoding the proteins are identified by the methods described in PROTEOLINK™ In Vitro Expression Cloning System kit (Promega, Cat# L6500).

EXAMPLE 14

Protease Assay

To detect proteases present in human blood or in a reticulocyte lysate expression system, a his-tagged protein that is a substrate for a protease is bound to zinc- or cobalt-charged solid support (e.g., a solid support prepared as described above in Example 1). The particle-bound his-tagged protein is incubated with reticulocyte lysate or human blood samples under the conditions described in Example 3 or 5 for a specific period of time. The solid support is washed and the his-tagged proteins are eluted as described above in Example 3, 5, or 7. Proteins are analyzed by SDS-PAGE, Western blot, or mass spectrometry.

In a separate experiment, his-tagged protein substrate is added directly to the rabbit reticulocyte lysate or human blood sample and incubated for specific period of time. His-tagged proteins are then purified as described in Example 3, 5, or 7. Protease activity is analyzed by SDS-PAGE, Western blot, or mass spectrometry.

EXAMPLE 15

Identification of Specific Protein Markers from Human Blood Samples

Specific protein modifications or protease assays may be used to screen for protein markers from human blood samples. For example, serum proteins may be analyzed to identify specific protein markers for prostate cancer (Lehrer et al "Putative protein markers in the sera of men with prostatic neoplasms" BJU Int. 2003 August; 92(3):223–5). Similarly, human blood samples could be analyzed by purified his-tagged proteins for the up or down regulation of specific kinases, proteases or protein modification systems. For example, a his-tagged kinase will be incubated with blood samples from a person with cancer and a person without cancer. After specific period of incubation, his-tagged proteins will be purified from the blood samples as described in Example 3 or 6. Purified proteins are then analyzed by mass spectrometry or gel analysis for studying the protein modifications.

EXAMPLE 16

Protein-Ligand Interaction Studies

His-tagged proteins purified as described in the preceding Examples are suitable for studying protein-ligand interaction. His-tagged proteins from a cDNA library or a specific his-tagged coding sequence of interest are expressed in rabbit recticulocyte lysate and interaction between an expressed protein and a ligand is detected using fluorescently labeled ligand. For example, an inhibitor for caspase protein may be identified by expressing his-tagged caspase protein in rabbit reticulocyte lysate and purifying the caspase proteins using a zinc charged solid support, such as zinc-charged NTA-modified silica magnetic particles. For screening a plurality of potential ligands, a multi-well method such as a 96-well plate is used. Prior to elution, the bound his-caspase is contacted with a fluorescently labeled inhibitor. The solid support is washed the proteins are eluted, and the eluted proteins analyzed using a fluorometer. A similar approach may be used for any protein or ligand, as well as in directed evolution studies.

EXAMPLE 17

Analyzing Post-Translational Modifications of Proteins

Zinc-charged metal chelating resins are used to isolate proteins expressed in rabbit reticulocyte lysate from a cDNA library or a single protein coding sequence, which are then evaluated for post-translational modifications. A his-tagged cDNA library is expressed in rabbit reticulocyte lysate, the tagged proteins are bound to a zinc charged solid support, washed, and contacted with a fluorescently labeled antibody that recognizes a particular post-translational modification (e.g., acetylation or phosphorylation). Alternatively, a non-labeled primary antibody is used and its interaction with a his-tagged protein is detected using a fluorescently labeled secondary antibody. The antibody-labeled his-tagged protein may be subsequently recovered as described above, and analyzed in fluorometer.

Zinc-charged solid supports may be used to isolate particular his-tagged protein substrates. For example, brain cDNA library encoding untagged proteins is expressed in GOLD TNT® SP6 Express 96 System (Promega Cat#L5800) or GOLD TNT® T7 Express 96 System (Promega Cat#L5600) as recommended by the manufacture. The lysate is contacted with a zinc-charged solid support to which a his-tagged protein or proteins is evaluated for modifications. The cDNA clone expressing the protein responsible for modifying the his-tagged protein is identified.

EXAMPLE 18

Antibody Based Detection of Proteins from Rabbit Reticulocyte Lysate

Fluorescent labeled antibodies can be used to detect his-tagged proteins expressed in rabbit reticulocyte lysate. This could be achieved by expressing and attaching the his-tagged proteins to a zinc charged solid support, followed by contacting with fluorescently labeled antibodies, washing, and detecting bound antibodies fluorescently.

EXAMPLE 19

Screening of his-Tagged Antibodies Using Fluorescently-Labeled Antigen

Rabbit reticulocyte-based cell free protein expression system is used to express antibody coding sequences and subsequent screening using fluorescently labeled antigens. In vitro antibody libraries are generated by directed evolution methods such as DNA shuffling, phage display, ribosome display, covalent display, mRNA display, or any other suitable method. Full length antibodies or antibody fragments including the antigen binding region are expressed with polyhistidine tags in a rabbit reticulocyte lysate expression system. The his-tagged antibody or antibody fragment is allowed to interact with a zinc charged solid support as described above for his-tagged proteins generally. Fluorescently labeled antigen is used to select the antibodies capable of interacting with the antigen to form an antigen-antibody pair. The method permits screening of large numbers of antibodies or antibody fragments in a high throughput manner.

EXAMPLE 20

Detection of Fluorescent Dyes Following Removal of Hemoglobin from Rabbit Reticulocyte Lysate Fluorescent compounds have been widely used for developing various functional assays such as kinase or caspase assays, for example. However, contaminating hemoglobin inhibits fluorescence of certain fluorescent compounds. The suitability of the zinc based purification system for use in assays employing fluorescent labels was evaluated using rhodamine 110 (R110) as follows.

Figure 11:
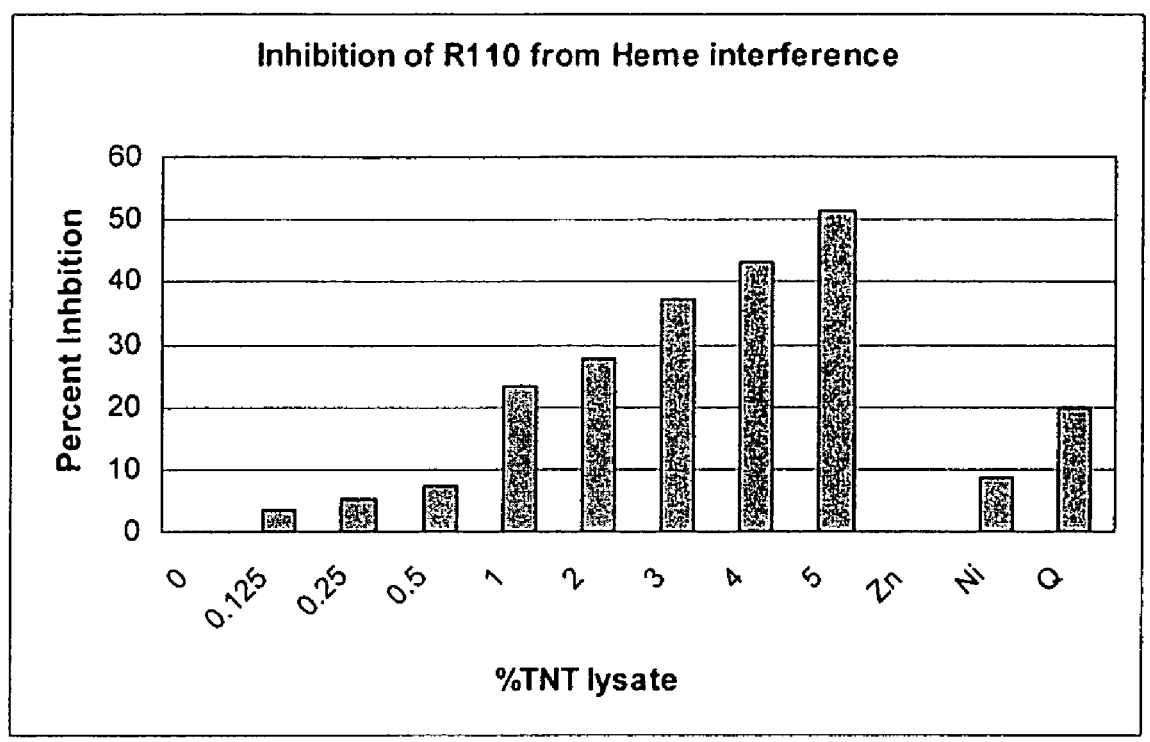
FIG. 11 is a graph showing percent inhibition of fluorescence of rhodamine R110 in the presence of hemoglobin.

Various dilutions of rabbit reticulocyte lysate (TNT® T7 coupled transcription/translation lysate (Cat#L1170, Promega Corp., Madison, W.I.)) were mixed with rhodamine 110 (R110) and the fluorescence was measured using a fluorometer (excitation 485; emission 530). In parallel, zinc or nickel charged particles were mixed with rabbit reticulocyte, without any his-tag protein. The particles were washed and treating with elution buffer as described above. The elution was mixed with R110 and the fluorescence measured using a fluorometer. The results are shown in FIG. 11. It is evident from this experiment that hemoglobin inhibits R110. Zinc charged resin removes hemoglobin from rabbit reticulocyte lysate so that the purified samples do not inhibit R110. The results are shown in FIG. 11. It is evident from this experiment that hemoglobin inhibits R110. Zinc charged resin removes hemoglobin from rabbit reticulocyty lysate so that the purified samples do not inhibit R110.

EXAMPLE 21

Evaluation of Fluorescence Based Caspase Assay Following Removal of Hemoglobin by Zinc Charged Solid Support The suitability of a using a fluorescence based caspase assay to detect activity isolated from rabbit reticulocyte lysate was evaluated as described below.

Rabbit reticulocyte lysate (TNT® T7 coupled transcription/translation lysate (Cat#L1170, Promega Corp., Madison, W.I.)) or water (40 µl) was combined with 100 µl 50 mM sodium phosphate containing 500 mM NaCl and 10 µg purified his-tagged caspase3 (Upstate, Cat#14–264). The mixture was incubated in a tube containing with 3 mg of zinc or nickel charged magnetic particles for 15 min on a rotary shaker at room temperature. The flow through was removed by magnetization. The particles were washed four times with 50 mM sodium phosphate +500 mM NaCl, and the caspase eluted with 100 µl 1 M imidazole. The eluted material was serially diluted (1:5, 1:10, 1:20, 1:40, 1:80, 1:160, and 1:320) with phosphate buffered saline to give a final volume of 100 µl. Caspase activity was dected using APO-ONE® substrate diluted in APO-ONE® buffer (APO-ONE® Homogeneous Caspase-3/7 Assay, Cat# G7792, Promega Corporation). The absorbance (λ=530) of each sample was measured was using a CYTOFLOUR® II (CytoFluor (Bio Research, Bedford, M.A.)). In this assay, the $A_{530}$ correlates with caspase activity.

Figure 12:
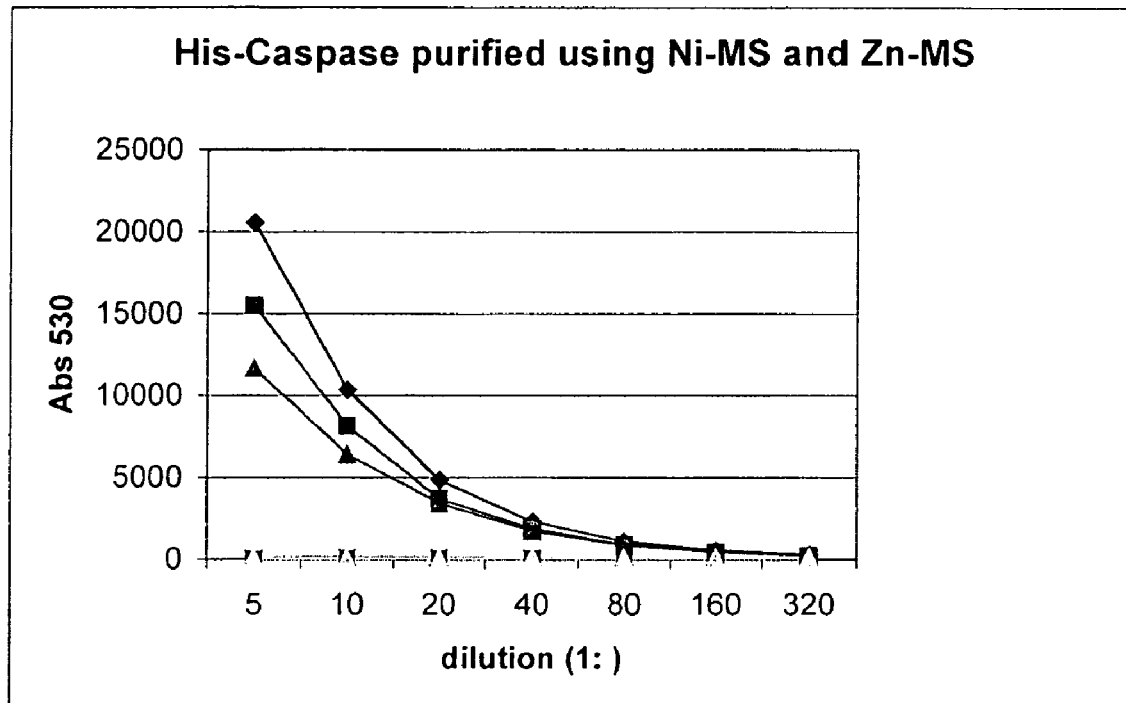
FIG. 12 is a graph showing activity of his-tagged caspase (as measured by fluorescence) recovered from rabbit reticulocyte using zinc or nickel charged particles.

With reference to FIG. 12, the $A_{530}$ for each sample, which correlates with the amount of active caspase present in the sample, was plotted as a function of the dilution factor: Absorbance of caspase purified from TNT® using zinc particles (diamonds); absorbance for caspase purified from water using zinc particles (squares); and absorbance for caspase purified from TNT® using nickel particles (triangles). As expected, samples containing only TNT®(no caspase) isolated on zinc or nickel particles had aborbances that did not exceed baseline.

The results show that zinc particles are useful for isolating his-tagged proteins from hemoglobin-containing starting materials (e.g., rabbit reticulocyte lysate or blood) for subsequent analysis in a fluorescence based caspase assay. This approach is suitable for in vitro screening of his-tagged caspases expressed in rabbit reticulocyte lysate expressed from a cDNA/mRNA library.

It is also envisioned that the caspase assay could be performed essentially as described above but using a luminiscence based assays (e.g., CASPASE GLO™ 9 Assay, Cat# G8210, Promega Corporation).

The invention claimed is:

1. A method of characterizing a his-tagged protein comprising:
    (a) contacting a starting material comprising the his-tagged protein and hemoglobin with a zinc or cobalt charged solid support under conditions that allow his-tagged protein to preferentially bind to the solid support, relative to binding to the hemoglobin;
    (b) washing the solid support;
    (c) contacting the his-tagged protein with a substrate or a second protein; and
    (d) detecting interaction between the his-tagged protein and the second protein or substrate to characterize the his-tagged protein.

2. The method of claim 1, wherein after step (b), the his-tagged protein is eluted from the solid support.

3. The method of claim 1, wherein the interaction is detected by detecting an increase or decrease in fluorescence.

4. The method of claim 1, wherein step (c) comprises contacting the his-tagged protein with a kinase.

5. The method of claim 4 wherein step (d) comprises characterizing the his-tagged protein for its ability to serve as a substrate for the kinase.

6. The method of claim 1, wherein step (c) comprises contacting the his-tagged protein with a protease.

7. The method of claim 6, wherein step (d) comprises characterizing the his-tagged protein for its ability to serve as a substrate for the protease.

8. The method of claim 1, wherein step (c) comprises contacting the his-tagged protein with a substrate.

9. The method of claim 8, wherein step (d) comprises detecting kinase activity of the his-tagged protein.

10. The method of claim 8, wherein step (d) comprises detecting protease activity of the his-tagged protein.

11. The method of claim 1, wherein step (c) comprises contacting the his-tagged protein with an antibody.

12. The method of claim 11, wherein the antibody is a fluorescent antibody.

13. The method of claim 1, wherein the his-tagged protein is an antibody and wherein step (c) comprises contacting the his-tagged antibody with an antigen.

14. The method of claim 13, wherein step (d) comprises detecting binding of the his-tagged antibody to the antigen.

15. The method of claim 14, wherein the antigen is fluorescently labeled.

16. The method of claim 1, wherein step (d) comprises detecting interaction between the his-tagged protein and a ligand.

17. The method of claim 16, wherein the ligand is fluorescently labeled.

18. The method of claim 1, wherein step (d) comprises detecting caspase activity of the his-tagged protein.

* * * * *